United States Patent [19]

Jacob et al.

[11] 4,438,541

[45] Mar. 27, 1984

[54] TOOTHBRUSH WITH HEAT SHRUNK SYNTHETIC FILAMENTS

[76] Inventors: Joseph Jacob, 1035 Washington St., Wooster, Ohio 44691; Charles J. Love, 1221 Tower Bldg., Lorain, Ohio 44053

[21] Appl. No.: 377,793

[22] Filed: May 13, 1982

Related U.S. Application Data

[62] Division of Ser. No. 946,608, Oct. 2, 1978, abandoned.

[51] Int. Cl.³ ............................................... A46B 9/04
[52] U.S. Cl. ............................... 15/167 R; 15/159 A; 15/187
[58] Field of Search ................ 15/167 R, 159 A, 110, 15/186, 187, 188

[56] References Cited

U.S. PATENT DOCUMENTS

| | | | |
|---|---|---|---|
| 1,179,426 | 4/1916 | Hamilton | 15/167 R |
| 3,337,893 | 8/1967 | Fine et al. | 15/167 R X |
| 4,030,845 | 6/1977 | Deckert | 15/167 R |
| 4,208,758 | 6/1980 | Timmis et al. | 15/159 A |

*Primary Examiner*—Peter Feldman
*Attorney, Agent, or Firm*—Ray S. Pyle

[57] ABSTRACT

The disclosure teaches a new method of dental plaque removal and the structure of a brush bristle which enables the method most efficiently. A filament loop of contractable material such as polypropylene is caused to shrink as it is being attached to a base. The loop exhibits an extraordinary contraction wherein the loop is not merely reduced as expected, but by the process of this invention it contracts into tightly adjacent filaments with a tight return loop. The resulting bristle not only solves the vexing problem of proper bristle polishing, but as an unexpected additional value, exhibits a greatly improved capability to actually scoop away tooth deposits such as plaque.

3 Claims, 4 Drawing Figures

TOOTHBRUSH WITH HEAT SHRUNK SYNTHETIC FILAMENTS

This application is a divisional application of parent application Ser. No. 946,608, filed Oct. 2, 1978, now abandoned.

BACKGROUND OF THE INVENTION

As a prelude to the full understanding of the problem area of dental health to which the present invention is directed, it is recommended that U.S. Pat. No. 3,905,113 be read and understood. This prior teaching presents a novel approach to dental care by enabling the user to maintain a tactile sense and thus feel more accurately where he is in the masticatory region.

The prior art has been directed toward the provision of bristles which scrub the plaque as they sweep away trapped food particles. The better brushes are processed to reduce fragmented end structures which lacerate tender gingivae.

THE PURPOSE AND OBJECTS OF THIS INVENTION

This invention retains all the advantages of prior U.S. Pat. No. 3,905,113. The purpose of this invention is to provide a novel bristle formation that fully eliminates fractured bristle ends and provides a superior brushing end.

The invention, in particular, relates to a discovery of a superior double bristle with a tight loop end having the configuration of an inverted U-shaped continuous filament which not only solves the problem of bristle ends, but actually provides a scooping action to cut free and carry away the tenacious plaque formation.

THE DRAWING

THE PREFERRED EMBODIMENT

This invention is a discovery which came through observation of the results obtained by novel tooth brushing structure of U.S. Pat. No. 3,905,113.

This prior patent describes a brush concept which is rapidly gaining acclaim as a means for improved cleaning of tooth surfaces, especially of plaque removal.

The bristles of the patent brush have been made on a loom which produces loops of filaments, and then as in conventional practice, the loops were severed to produce individual bristles.

During the preliminary testing, its was concluded that the cut filaments were too sharp and jagged for continued use on gum tissue. Hence the bristles were polished, but were not of sufficient quality to meet the high standards demanded by the inventors.

One of the materials considered for bristles was polypropylene, which is well known for its heat shrink characteristic. However, if subjected to heat without the process of this invention, the loops would merely contract into very resilient loops incapable of producing any useful scrubbing pressure. Also, flexible loops destroy the erect attitude which will transmit pressure through to the base end, which is one of the major tenants of the prior U.S. Pat. No. 3,905,113.

Figure 1:
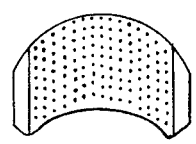
FIG. 1 is a plan view of one preferred embodiment of a brush tool utilizing the novel bristle structure.
Figure 2:
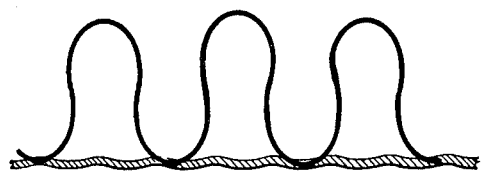
FIG. 2 illustrates a fabric ground base and loops of heat shrinkable filaments as they appear when merely woven.
Figure 3:
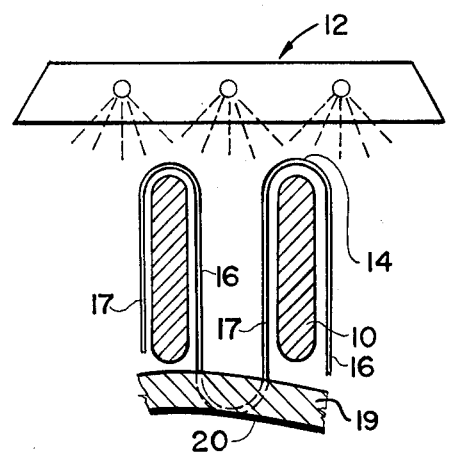
FIG. 3 illustrates the use of forming bars in the weaving process and the application of heat to cause the filaments to contract to the bars.

As shown in FIG. 2 of the drawing, the loops have no distinct side portions or scrubbing ends. They will simply flex under any pressure, and fail as scrubbing bristles.

Observation of the nature of heat shrink wrapping materials developed into the conception of the present invention. A test was made. The loops were woven over elongated forming rail 10 and simultaneously heated by radiant source 12.

The result was a spectacular accomplishment in the form of a tight return bend 14 over the top of the rail 10 and side lengths 16 and 17 held in a substantially straight rod formation. When this heat shrunk loop is removed from rail 10 it retains the formation illustrated in FIG. 4. The actual small bristle exhibits a much superior erect resiliency than would be possible by a mere loop structure, whether heat shrunk or not. The bristles resiliency is controlled by selection of filament diameter and height of the column. The best results appear to be obtained with about 0.007 to 0.009 inches in diameter filaments and a loop about 0.175 to 0.195 inches high.

Study of this composite bristle under magnification brought about a question of whether the naturally formed end could serve as a polished end without cutting and polishing.

Figure 4:
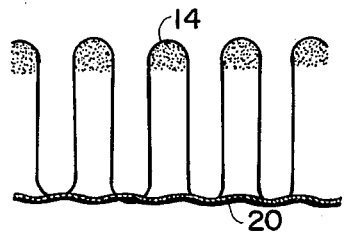
FIG. 4 is a greatly enlarged section showing the structure of the new bristle with trapped plaque material in the loops.

It was then discovered that a truly unique brush bristle had been developed. The bristle, in use, has been found to not merely scarf the surface of a tooth in a superior manner, but microscopic study has shown that the return end acts as a scoop to cut into the plaque deposit and actually carry it away to a far greater extent than prior entrapment. Illustration of plaque entrapment is difficult in a line drawing. FIG. 4 is a representation made from an enlargement of a photograph. The shaded areas represent entraped plaque material as seen in an actual photomicrograph. An analogy may be made to the action of a kitchen scrub pad which actually entraps food and is later flushed free. The bristle ends will clean in the same manner as a tooth brush will clean teeth. The entrapment and scoop action is a valuable additional value produced by this invention in addition to the novel method of producing an excellent bristle end.

The inventors are aware of the desirability of the bristles to extend into the gingival sulcus. With the configuration and tightness of the loop, it has been discovered that this characteristic is retained and even improved because of the scooping action of the loop. When employed as taught in U.S. Pat. No. 3,905,113, by spreading over the gentle curve of the finger, the bristles being of the same length, follow the contour of the finger and bring to bear a variety of pressures utilizing a multiple action of scouring, scooping, and stimulating of tooth and gum tissue.

This structure, as in U.S. Pat. No. 3,905,113, has a base fabric 19 woven with the bristle loops and has applied to the bottom surface thereof a layer of pressure sensitive adhesive 20 to attach the appliance to the finger. The greatly enlarged drawing exaggerates the irregularity of this layer.

However, it is recognized that the structure, in various size filaments and bristle heights can serve a wide range of brush functions. For example, conventional tooth brushes, a dish washing tool, or a scrub brush. Also, the tooth brush configuration has been well accepted by veterinarians for cleaning dog teeth. The dog will not exhibit fear of the brush on the finger of the veterinarian, and the bristles can be structured with the proper resiliency for dog teeth.

What we claim is:

1. A toothbrush having a base and a plurality of bristles, each of which is composed of a heat shrunk synthetic filament held in a single composite inverted U-shaped configuration by two lengths of straight, substantially parallel, closely spaced side legs and a return bend, the side legs and return bend of each bristle being contracted to a reduced size from being heat shrunk while held over a form rail so as to form tightly adjacent filaments with a tight return bend, whereby each bristle acts as a dry scoop to cut into and scarf away dental plaque.

2. A toothbrush, as defined in claim 1, said plurality of filaments each being about 0.175 to about 0.195 inch high and with a short, tight, top loop and substantially parallel straight side legs closely spaced, characterized such that the loop lacks sharp or broken fragments and is effective to scour, scoop and stimulate tooth and gum tissue without irritation thereof.

3. A toothbrush as defined in claim 1, wherein the bristle filament is heat shrunk polypropylene of a diameter of about 0.007 to about 0.009 inch.

* * * * *